(12) United States Patent
Epstein

(10) Patent No.: US 6,987,659 B1
(45) Date of Patent: Jan. 17, 2006

(54) PLUG AND CIRCUITRY FOR GROUNDING AN ELEMENT

(76) Inventor: Barry M. Epstein, 3 Milford Pl., Dallas, TX (US) 75230

( * ) Notice: Subject to any disclaimer, the term of this patent is extended or adjusted under 35 U.S.C. 154(b) by 278 days.

(21) Appl. No.: 10/112,952

(22) Filed: Apr. 2, 2002

Related U.S. Application Data

(63) Continuation-in-part of application No. 09/934,047, filed on Aug. 22, 2001, now Pat. No. 6,873,516.

(51) Int. Cl.
*H02H 1/00* (2006.01)

(52) U.S. Cl. ...................... 361/220; 361/212
(58) Field of Classification Search ......... 361/212–224
See application file for complete search history.

(56) References Cited

U.S. PATENT DOCUMENTS

| | | | | | |
|---|---|---|---|---|---|
| 3,699,562 | A | * | 10/1972 | Kelly ........................ | 340/649 |
| 3,733,576 | A | * | 5/1973 | Cooper ...................... | 439/103 |
| 3,924,914 | A | * | 12/1975 | Banner ....................... | 439/15 |
| 3,988,639 | A | * | 10/1976 | Preiser et al. ................ | 361/58 |
| 4,118,690 | A | * | 10/1978 | Paynton ..................... | 340/656 |
| 4,313,148 | A | * | 1/1982 | Turner ....................... | 361/212 |
| 4,493,515 | A | * | 1/1985 | Banks ........................ | 439/97 |
| 4,586,106 | A | * | 4/1986 | Frazier ...................... | 361/212 |
| 4,654,746 | A | * | 3/1987 | Lewis et al. ................. | 361/212 |
| 4,756,593 | A | * | 7/1988 | Koakutsu et al. ............ | 385/139 |
| 4,875,148 | A | * | 10/1989 | Roe et al. .................... | 363/41 |
| 5,115,368 | A | * | 5/1992 | Smith ......................... | 361/56 |
| 5,686,897 | A | * | 11/1997 | Loh ........................... | 340/649 |
| 6,003,234 | A | * | 12/1999 | Seibert ....................... | 33/371 |

* cited by examiner

*Primary Examiner*—Stephen W. Jackson
*Assistant Examiner*—Danny Nguyen
(74) *Attorney, Agent, or Firm*—Terry M. Gernstein

(57) ABSTRACT

A plug includes an element that is electrically connected to a ground element in a receptacle in a set up configuration and an electrical connection that is attached to an element to be grounded whereby an element, person, or device, or the like, can be securely grounded using the ground circuit in a receptacle. Grounding is via a suitable signal circuit in one form of the invention.

20 Claims, 7 Drawing Sheets

PLUG AND CIRCUITRY FOR GROUNDING AN ELEMENT

CROSS-REFERENCE TO RELATED APPLICATIONS

The present application is a continuation-in-part application of patent application titled SYSTEM FOR PROTECTING A PERSON FROM THE EFFECTS OF ESD, Ser. No. 09/934,047, filed on Aug. 22, 2001, now U.S. Pat. No. 6,873,516 by the same inventor and currently pending an and incorporates by reference the disclosure of co-pending application titled GROUNDING ELEMENTS FOR ELIMINATING ESD FROM FLOOR COVERINGS AND DEVICES filed by the same inventor concurrently herewith.

TECHNICAL FIELD OF THE INVENTION

The present invention relates to the general art of electrical systems and devices, and to the particular field of discharging or preventing accumulation of electric charges.

BACKGROUND OF THE INVENTION

The problem of electrostatic discharge (ESD) is well known. From merely receiving a mild shock after crossing a room and touching a metal object, to sending a shock into electronic equipment, nearly everyone has experienced an ESD problem at some time.

While static electricity is extremely complex, several overall theories are generally accepted with regard to the action of ESD. Static electricity charges on a person or object are generally like charges. As such, as static electricity charges build up on a person or object, these charges tend to migrate as far apart from each other as possible as determined by the geometry of the person of object. Thus, for example, it is common for static electricity charges to migrate to a person's fingertips. For this reason, when that person reaches out to touch an electrically conductive object, a spark will jump when the gap between that person's fingertips and the object based upon the potential difference between the fingertips and the object. This discharge is very rapid and can be quite violent. If the electrically conductive object is sensitive electronic equipment, that equipment may be damaged either from the magnitude of the discharge and/or from the speed of the discharge. At the least, the charge could cause the equipment to execute an error. A sufficient number of such discharges may eventually damage the equipment.

Accordingly, the art contains many inventions intended to protect the equipment or the person from the effects of this sudden, and sometimes violent, discharge associated with ESD.

For instance, in the logging industry where chains are lowered by helicopter to loggers waiting on the ground to fasten fresh-cut timber to them so it could be airlifted to the sawmill or nearby waterway, track access point or the like, the loggers are often reluctant to grab the chain because of a painful shock that may occur as a result of a buildup of static electricity which will be discharged to ground through their bodies. This particular problem has been solved by incorporating a resistance in the line from the charge-carrying object, such as the helicopter, to the person on the ground. The high resistance causes the current to be low enough that the discharge will not be painful.

However, this is cumbersome. This solution may be even more cumbersome if the person is an office worker who moves around a great deal. Accordingly, this solution to the ESD problem has serious shortcomings.

Accordingly, there is a need for a system that protects a person against the effects of ESD but can do so in a manner that does not interfere with any task the person may be performing and further will not be cumbersome or burdensome for the person to use.

Still other inventions are directed to protecting electronic equipment from the effects of ESD. For example, many computers include touch pads or touch areas for the user to touch before touching the remainder of the computer. The touch pads are grounded so the ESD will pass from the person via a spark or the like directly to ground without going to or through the computer.

While many of these devices work well, there are several problem areas not addressed thereby. This results in drawbacks and disadvantages for such devices when a person or equipment are situated in certain environments or subject to certain conditions.

First, no matter how effective a touch pad is it will be totally ineffective if the person does not use it. That is, if the person carrying a large ESD charge forgets to touch the touch pad and proceeds to touch a computer, the ESD will discharge through the computer and the touch pad will have been useless. Thus, a shortcoming of such touch pads is that they require the person to remember to use it.

Furthermore, no matter how effective the ESD protection device is, the current level and/or the change in current level may be so high that either the person or the equipment can be damaged.

Still further, while placing a touch pad on a computer may protect the computer it does not protect the user from the effects of an electrostatic discharge.

As mentioned above, the majority of applications for the prevention of ESD are in the manufacturing or medical fields and are largely concerned with protecting the 'manufacturing' process or sensitive components for ESD damage. Examples include moving mediums such as the manufacture of rolls of paper, the assembly of delicate electronic chips and circuitry and surgeon-patient contact during an operation.

An analysis of each of the above will help illustrate the shortcomings of the prior art. In the manufacture or printing of paper, long rolls of paper may move at high speed. Often the path may involve rubber or other rollers and guides. As the paper rubs across such items a static electricity charge may be generated. Since the paper path is well controlled, it is an easy process to place grounded conductive brushes or flat metal springs in contact with the moving paper since the paper stays in a fixed path. Such electrodes are connected directly to the grounded frame of the associated machinery or to another path eventually leading to earth ground or other equalizing means.

Another common application of ESD control is in the production or repair of fragile electronics such as computer circuit boards. Even a slight electrostatic discharge through a sensitive device may destroy it. Therefore, significant effort and cost is devoted to eliminating the possibilities of electrostatic potentials in the vicinity of the sensitive electronics. Typically, a single ground point is provided that all associated elements are connected to so that no electrostatic potential can exist between them that might flow through the sensitive electronics. For example, a conductive floor mat is provided that is connected to the ground point, or a work surface mat that is conductive (or dissipative) is also provided that is wired to the same ground point, the work table frame and any test equipment is connected to the same point, finally the assembly person is also connected to the same point, typically by a wrist strap tether. The tether generally consists of a wrist pad and grounding wire that is eventually connected back to the single ground point. For operator safety, the ground wire typically contains a 1 Meg resistor to limit current flow to safe levels should the operator come in contact with 120 volts AC. This tethering restraint is inconvenient and not considered suitable for a typical office worker or call center operator. The single ground point is eventually connected to true earth ground or other equalizing point by another conductor.

Applications are similar in the medical field, employing similar tethers and/or foot/shoe connectors also considered impractical for the typical office worker environment.

Today, a new set of ESD problems is emerging in the typical work place or home office environment. Today, a typical worker may exist in a virtually electrically isolated environment—a plastic computer case, plastic keyboard, plastic control knobs on a molded plastic control panel, plastic office chair with man-made fabric and plastic wheels, non-conductive flooring or carpeting and even a headset with foam or molded plastic earpieces and plastic microphone tube.

As the operator moves in his/her chair, there are many opportunities for a very large electrostatic charge to build up on his/her body. Friction between dissimilar materials is the classical means for generation of electrostatic voltages. There are many such situations that exist continually in the operator environment today-the operator's clothing sliding against the chair back or arm rests, the operator's shoes sliding on the carpet, the plastic chair wheels sliding against the carpet are a few examples. The effects can be cumulative over a long period of time, and can become quite high.

Eventually a discharge or equalization to (true earth) ground must take place. The higher the value of the electrostatic voltage charge, the greater the distance the charge may 'jump' to discharge, and the more 'catastrophic' the event to the operator. For example, there are many documented cases of operators in call centers experiencing a very loud pop or explosion in their ear, ear pain, and even bleeding in the ear as the discharge path appears to take place through the operator's headset. Other documented cases include severe neck pain, nausea, numbness, elevated blood pressure and rapid heart beat.

There are many possibilities as to why these effects are worse than the typical nuisance static electricity charges walking around the house. For instance, the discharge path may be more surprising or appear worse to the user if it involves the user's ear. Recently, this has been attributed to electrostatic discharge of the operator with the grounding mechanism being the metallic portion of the ear piece coupled to its metallic conductors and eventually to earth ground through its associated electronics. This may be a direct low impedance ground or it might be a higher impedance which is still sufficiently low with respect to that needed to successfully equalize the static charge. Still in other cases, as explained below, the associated electronics may potentially make the discharge injury to the person more severe and disturbing by causing a high current pulse to take place as the discharge event. This effect may be further compounded by allowing the operator to be exposed to other voltage or leakage paths developed via the ear over time.

In some cases, the associated electronics may experience physical damage or processing disturbances due to the operator electrostatic discharge. For example, the headphone circuit might involve a transformer with a 600 to 10,000 volt breakdown rating between its windings (connected to the headset diaphragm) and conductive metal core. However, the electrostatic voltage on the operator may exceed 15,000 volts-far more than the design tolerance of the transformer. Should the transformer be exposed to such excessive high voltage, a 'breakdown' or 'shorting' may occur. Thus, the operator electrostatic voltage might cause a 'short circuit' insulation breakdown or lower resistance to develop between the headset winding (secondary) and primary winding which may be at a constant high voltage level with respect to ground or the transformer core which may be connected to earth ground, thus completing the discharge path.

The transformer breakdown may cause a permanent equipment failure. Other equipment damage or errors can also occur due to the electrostatic discharge event. The electrostatic discharge event may cause an electromagnetic or radio frequency pulse to be generated. This pulse may radiate into nearby circuitry causing errors in processing or noise in audio or video circuits. Although a transformer discharge event has been described above, other similar discharge paths can be envisioned, with similar catastrophic results.

With continued miniaturization of electronics, the problems may become more severe as circuit component voltage tolerances become less and enclosure insulation distances become less.

Accordingly, there is a need for an ESD protection system that protects a person and electronics from the effects of ESD, even if that person is in an environment that is intended to nominally insulate that person from ground.

As the cost of doing business increases, many businesses are reluctant to purchase new original equipment. Thus, it is most advantageous if existing equipment can be easily modified or retrofit to achieve new and improved results. This is the situation with protecting people from the effects of ESD. Thus, there is a need for a system for protecting people against the effects of ESD that can easily be retrofit onto existing equipment.

The parent application Ser. No. 09/934,047, the disclosure of which is incorporated herein by reference, discloses an overall system for overcoming the above-discussed problems.

In addition to the above-discussed problems, there are many situations that require a means for conveniently grounding electronic equipment beyond the safety requirements of the National Electric Code (NEC). Not only is grounding required to overcome problems associated with ESD, grounding is often required for safety reasons. The NEC requires that all new general purpose receptacles, for example, contain a grounded conductor.

Therefore, there is a need for a means to properly ground elements to not only overcome problems associated with ESD, but to meet NEC requirements as well.

Typically, the ground used to satisfy NEC requirements is the "round" hole on the standard home or office receptacle and many plugs have a prong to make contact with that ground element to provide safety grounding to attached equipment. Like the safety provisions of a high voltage conductor and prong, this grounding prong also is protected from casual access when a plug is plugged into the receptacle. Thus, there is no convenient access to the ground conductor for many common situations.

Therefore, there is a need for a means for providing convenient access to the ground conductor of many receptacles.

The need for grounding can be illustrated by two examples: the home theater and the above-discussed ESD fields. In the home theater, most devices such as a source (FM tuner, DVD player, and the like) are connected to preamplifiers or even amplifiers by inexpensive shielded cables. In some cases, such as when amplifiers are co-located with speakers, these cables can become quite long and the signals are very low level. Thus, they are susceptible to "hum" and "noise" being picked up over the cable. Often, the source of the hum or noise will be from currents traveling along the ground conductors of the cable (typically the shield) and coupling the noise into the signal path. The currents may originate because of lack of consistent grounding on all connected devices. This may be because different outlets are used, extension cords without a third wire ground are used, or many audio/video components come with only a two-prong plug without a ground which is typically a third prong. There are almost always minute currents in such devices wanting to travel to true ground. Thus, if one device is grounded and others are not, ground "leakage" currents will tend to flow through the signal cables to the grounded device and in the process cause what is typically called sixty cycle hum or other noise. This leakage ground current situation is illustrated in FIG. 1. There may be ungrounded source devices UD such as DVD players or VCRs. A central preamplifier PA, common to many ungrounded devices may be grounded as shown by the third wire TW on a power plug PP. Leakage currents, li, from the ungrounded devices flow along a common (shield) conductor CC of the signal cable and can be cross-coupled into the signal path. Charge built up by ESD can also flow in the same manner.

In many cases, the lack of a convenient fool-proof ground leads to a potentially dangerous or lethal situation. One typical situation is in the ESD field, although it will be understood by those skilled in the art that other situations can occur, includes a person purchasing a ring terminal and using it incorrectly. The inventor has been aware of ESD equipment distributors improperly advising their customers with the result being dangerous and frightening electrical arcing taking place along with potentially lethal situations.

As mentioned above, one common ESD application is to provide personnel with a grounded wrist strap to ground their body, thus dissipating any electrostatic charge built up in their body before it might damage sensitive electronic equipment they may be repairing or building. A grounding kit K is shown in FIG. 2 and might include a ground wire GW leading to a disconnect plate DP. The ground connection provided for the wire is typically a bare exposed metal ring terminal RT. Disconnect plate DP, shown in end view in FIG. 2, may be mounted under a front edge of a user's work table so that a wrist strap WS connection can be easily connected or disconnected. Typical "banana plugs" BP are used for the connection at the disconnect plate. These are designed for signal, not electrical power, applications and hence have none of the safety features required for electrical power connectors. Connections are typically exposed on both the front and the rear of the plate. If these connections become charged with the typical one hundred twenty volts of commercial electrical power, it could be dangerous to the user. In addition, the wrist strap to the user generally contains a one meg resistor in its electrical path to limit current to a safe value should the source wire come in contact with one hundred twenty volts. Somehow, if someone wired around the resistor or the strap or grounding element does not contain a resistor a potentially lethal situation could exist if the source comes in contact with one hundred twenty volts. The ground wire on these kits typically is terminated with an uninsulated ring terminal. Ground wires with similar terminals are sold in many other consumer situations such as to ground computer monitor shields.

It is an improper application of this ring terminal which leads to many dangerous situations. It is designed to be installed under a grounded screw in a safe manner by a qualified electrician or other such person skilled in the art. If, for example, a ring terminal is merely placed on the ground prong of a three prong plug, contact could be made with the hot conductor but not ground. FIG. 3A shows an end view of a typical plug P and ring terminal RT'. In the case illustrated in FIG. 3A, high voltage from one of the connectors C is exposed in a dangerous manner at the disconnect plate via ring terminal RT' and subsequent locations such as the user's wrist strap or other devices which are believed by a user to be grounded. It is also conceivable that a user might simply attempt to stick the ring terminal into the "hot" conductor hole of the receptacle or two wire extension cord resulting in a dangerous situation.

Correct use of the ring terminal would be to place it under a ground screw. Often, this is the center screw of the cover plate of a standard duplex receptacle or screw on the metal body of a computer case or grounded piece of electrical equipment. However, today there are fewer availabilities of such ground screws. Most of the receptacles used in the millions of work stations today are a combination of press fits and molded assemblies without exposed ground screws. An example of such a situation is illustrated in FIG. 3B for receptacles MR. Thus, there is no easy way to properly ground in the field in many environments.

Thus, there is a need for a device for easily properly grounding in the field in most work environments.

Most computer cases today are plastic without exposed ground screws on the case. However, most connectors on the computer, such as the mouse plug and receptacle contain a ground conductor but there is no convenient way to use it for general or special-application grounding purposes.

Some applications, such as electrostatic discharge, require grounding to eventually discharge a static charge to true ground. The average current flows are very low and the impedance to ground can be quite high, well in the megohm range. This affords many additional opportunities for ground paths that would not be acceptable for or meet the requirements of typical electrical safety grounding where the ground system must be capable of supporting tens or hundreds of amps until a circuit breaker can shut down. For purposes of this disclosure, such paths will still be referred to as ground paths.

OBJECTS OF THE INVENTION

It is a main object of the present invention to provide a carefully controlled ground discharge path.

It is another object of the present invention to provide a ground discharge path that minimizes radiated disturbances to nearby equipment.

It is another object of the present invention to provide a discharge path that minimizes conducted disturbances to interconnected equipment.

It is another object of the present invention to provide a convenient earthing or equalization means.

It is another object of the present invention to support other work necessities of the operator such as operation of a computer mouse, keyboard, track ball or similar needs.

It is another object of the present invention to provide a grounding means via an existing ground of the associated electronics limiting the discharge current to a minimal value and waveshape so the operation of the associated electronics is not degraded.

It is another object of the present invention to provide an ESD suitable grounding means via existing signal conductors of the associated electronics limiting the discharge current to a minimal value and waveshape so the operation of the associated electronics is not degraded.

It is another object of the present invention to provide a convenient connection means for retrofit or connection in the field to existing systems by an unskilled person.

It is another object of the present invention to protect a person from the effects of ESD without requiring that person to wear any cumbersome wearing apparel.

It is another object of the present invention to protect a person from the effects of ESD without requiring the person to remember to carry out any special operation.

It is another object of the present invention to prevent or reduce an uncomfortable, disturbing or harmful electrostatic discharge to a person.

It is another object of the present invention to prevent or reduce an electrostatic discharge that might interfere with a person's ability to carry out his or her job.

It is another object of the present invention to provide a system to equalize (drain or discharge) an electrostatic charge from a person in a safe, harmless, nonnoticeable or minimally noticeable manner.

It is another object of the present invention to provide a contact surface to the person that is compatible with their normal (workspace) environment and provides discharge contact in the normal course of the operator's activities.

It is another object of the present invention to minimize the static shock that may take place upon initial contact by a prior-charged person.

It is another object of the present invention to provide retrofit kits compatible with control apparatus or other touch means applicable to the particular work set up to protect against ESD.

It is another object of the present invention to provide retrofit kits which can include a contact element, such as a plate, mat, faucet, handle, keyboard key, mouse, mouse pad, headset, microphone, or any of the items mentioned in this disclosure, the circuit elements mentioned in this disclosure and a connection element such as mentioned in this disclosure for connecting the assembly to ground or ESD-suitable ground.

It is another object of the present invention to protect a person from the effects of ESD.

It is another object of this present invention to define a mini version of the system of the present invention to stop or reduce nuisance shocks around houses or the workplace. For example it may mount on light switches, metal door frames, file cabinets, frames of modular office panels, front of stereo equipment or any electronic equipment where user is otherwise isolated from natural discharge paths prior to the time of contact.

It is another object of the present invention to provide a system for protecting a person against the effects of ESD using a simple plug-in jack to connect the system to any of the devices mentioned in this disclosure as a retrofit or add-on to protect a person against the effects of ESD.

It is another object of the present invention to provide a system that will be useable with a headset to protect a headset user from the effects of ESD.

It is another object of the present invention to provide a system that will be useable with a headset to protect a headset user from the effects of ESD without interfering with the operation of the headset.

It is another object of the present invention to provide a system that will protect a person from the effects of ESD and which can be releasably connected to a device that will be contacted by the user.

It is another object of the present invention to provide a system that will protect a person from the effects of ESD and which can be used in connection with an electrical plug.

It is another object of the present invention to provide a convenient, consistent and safe grounding system.

It is another object of the present invention to provide a convenient, consistent and safe grounding system that can be used by an unskilled person.

It is another object of the present invention to provide easy access to available ground conductors of specific configurations of conductors, such as power conductors.

It is another object of the present invention to provide easy access to available ground conductors of specific configurations of conductors, such as signal conductors.

It is another object of the present invention to provide a convenient system for connection one or more conductors relating to equipment or objects desired to be grounded.

It is another object of the present invention to provide current limiting safety in situations where high-impedance grounding is acceptable.

It is another object of the present invention to provide current limiting or wave shaping to limit the disturbing effects of ground currents on sensitive equipment while still providing grounding.

It is another object of the present invention to provide current limiting or wave shaping to limit current flows from ground which might be harmful to a person or equipment while still providing desired grounding.

It is another object of the present invention to provide multiple grounding provisions containing isolation between them or other characteristics as required or permitted by a specific application.

It is another object of the present invention to provide an adapter configuration with complementary male/female connector configurations so a receptacle can be used for grounding and still be available for other uses.

It is another object of the present invention to provide a safe means for attaching a grounding conductor to a receptacle.

It is another object of the present invention to provide a secure means for attaching wiring connecting to devices to be protected.

It is another object of the present invention to provide circuitry in applicable cases to enhance human safety and/or reduce ground currents which might cause equipment upset or damage.

It is another object of the present invention to provide a plug with optional test circuitry to verify performance or wiring quality.

It is another object of the present invention to provide a circuit which can be used to provide suitable ESD dissipation in cases where there is not a convenient typical low impedance ground present.

SUMMARY OF THE INVENTION

These, and other, objects are achieved by a plug for use in a circuit for protecting a person from effects of improper grounding which comprises an electrical conductor that is attached to an element to be grounded in a set up configuration, a ground, such as the ground provided in a receptacle, a plug housing, an electrical connector on the plug housing and electrically connected to the ground in the set-up configuration and which is electrically connected to the electrical conductor in the set-up configuration.

One application of the plug of the present invention is in dissipating ESD in the system disclosed in the parent patent application which discloses a system which protects a person from ESD by reducing static charges on a person to low levels on a periodic basis as the charges are built up. Specifically, convenient, casual grounding elements are provided to periodically reduce static electric charges from building up on operators of insulated equipment in an insulated environment until a severe, often painful or harmful, static breakdown occurs in an uncontrolled manner. The system disclosed in the parent application provides an ESD conducting contact element which is contacted by a user on a periodic or continuous basis and often in a time extended manner of more than 0.1 second (as opposed to a simple fast touch) and which has a very high resistance between the contact and ground. The contact element can be a single area of a user-contacted element or the user contacted element can have several areas. The user contacted element can be in several forms, including a computer mouse, a mouse pad, headphones, a computer keyboard, a joystick, a control knob or the like. It is noted that for purposes of this disclosure, the word conductive will be used to refer to the electrostatic discharge contact area being discussed in the general sense unless otherwise noted. In the true sense of the ESD definition that term means all but insulators. In the strict ESD discussion, conduction typically refers to resistances of 0 to 0.1 megohm, dissipative typically refers to 0.1 megohm to about $10^{12}$ ohms, and above that as insulative or non-conductive. A combination of two or more of the following is provided: convenient personnel contact means, current limiting means, and grounding path are provided. The current limiting means may contain series elements of high resistance and/or inductance. The inductance is to limit the development of radiated or conducted high frequency, high impulse leading edges of current or voltage which may upset or damage nearby or connected electronics. The high series resistance further limits total current to a value such that static electric charges are not significant if superimposed upon logic or logic ground conductors. Geometry of the personnel contact means (such as pads or electrodes), and the series resistor values are further selected to minimize the magnitude of uncomfortable personnel static shock. The high resistance also limits current flow to the user if instead of ground the ground wire comes in contact with a high voltage source. The value of resistance can be quite high since the goal is merely to reduce the static charges to low levels (for example 500 volts or less) on a periodic basis of minutes or hours as the charge is built up. However, the large resistance prevents a person from receiving a significant shock if they have a charge when they initially contact the contact element. That is, the large resistance is a balance between actually connecting a contact point to a grounding circuit (which would provide a path for a significant walk-up shock to occur) and preventing a walkup shock by "isolating" the contact device from the grounding circuit. Points of contact to the user are designed to be those that the user touches continually or intermittently in the normal course of operation so that bleeding of ESD can occur on a periodic or continual basis. Examples may include conductive mouse pads, conductive elements on the surface of a computer mouse or computer keyboard, trackball, conductive knobs or elements on a mic mixing panel, conductive elements on the headband or earpieces of a headset worn by the user, often used controls or touch points on virtually any type or user-operated equipment. A convenient earthing means is provided to drain off the static current so the charge may be effectively equalized.

If discharge methods are not used, the static discharge might build up for minutes or hours reaching very high values. The eventual uncontrolled discharge might take place in the user's ear to the metallic diaphragm inside the earpiece. The event may be frightening to the user.

The plug or a plug connector of the present invention can include a control circuit and the user-contacted element can be electrically connected to the plug or to the plug connector. The plug of the present invention includes means for conveniently and safely connecting a circuit to a ground element whereby true ground can be ensured for a circuit.

BRIEF DESCRIPTION OF THE DRAWING FIGURES

FIG. 3B illustrates prior art receptacles in modular office elements, such as modular office furniture or the like.

DETAILED DESCRIPTION OF THE PREFERRED EMBODIMENT OF THE INVENTION

Figure 1:
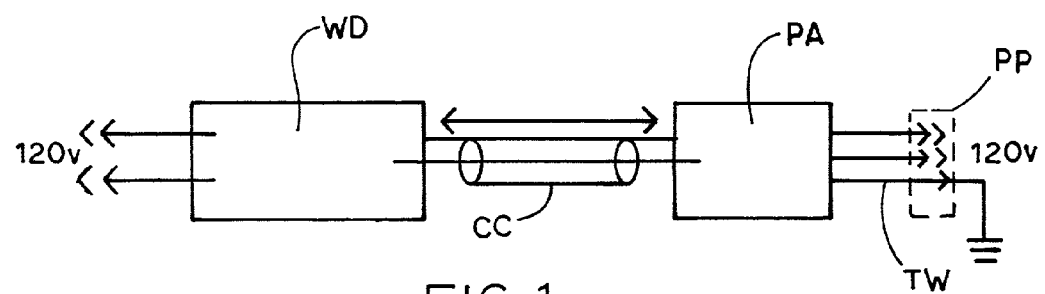
FIG. 1 is a block diagram illustrating leakage problems with prior art systems.

Other objects, features and advantages of the invention will become apparent from a consideration of the following detailed description and the accompanying drawings.

The plug embodying the present invention provides a secure and safe contact to ground for any element, including a human being. The plug of the present invention thus provides proper grounding that satisfies both NEC requirements as well as dissipates ESD.

While ESD is fully discussed in the parent application, and such discussion is incorporated herein by reference, since the plug embodying the present invention has applications in protecting a person from unwanted effects of ESD, in the interest of completeness, such discussion will be presented here. As discussed in the parent application, the build up of static charge on an individual generally takes place over time in many workplace environments. It may occur due to continued friction between shoes and carpet, clothing and chair, etc. Thus for protection it is necessary to provide a means of contact to a person's bare skin that is both casual and frequent during the work shift. Research and experience indicates that this should be every few minutes or so. Most individuals do not feel a discharge shock of 2000 volts or less and experience indicates that voltages may be building to the 5000 volt, 10,000 volt or more range before breakdown occurs. Generally, the operator is at his/her work position for an hour or more before the breakdown occurs.

Such breakdown may be considered as potentially disturbing to both the person and equipment, far more so than the typical nuisance discharge experienced when walking across a carpeted floor in the winter and touching a door knob. For example, there are cases of shock experienced when reaching for the "mute" button on an operator's telephone or from the user's ear through the metal parts of a headset worn by the operator.

There are many documented cases of this last occurrence requiring paramedic medic attention for weakness, blurred vision, high blood pressure, increased heartbeat, etc. There appears to be two reasons why this is more severe than the typical doorknob shock: (1) the electrostatic buildup may take place for a long time before breakdown occurs and hence be of greater magnitude than the typical carpet charge; (2) if discharge occurs at the ear, the associated sound may appear very loud to the operator, further adding to the perceived severity of the shock.

Generally the minimum discharge voltage a person can perceive is about 2000 volts. For purposes of this discussion an electrostatic voltage of 10,000 volts is assumed as a walk up initial voltage when first touching the ESD protective mat and is the voltage that will be used in the following discussion.

In many workplace applications, metal grounded surfaces have historically been used as a zero resistance to ground is common and considered safe. However, the initial walk up discharge shock in such a case can be very significant and disturbing. The shock is significant because significant electron flow takes place due to the obviously large number of electrons available in the earth for neutralization. A similar shock also takes place when touching large metal objects because of the large number of electrons available in the object for discharge. This invention limits the initial electron flow in two ways:

The discharge current is minimized by the series resistance of the control circuit and inherent resistance of the mat. A resistance of approximately 10 meg ohms or greater has been determined to be sufficient to minimize these initial shock effects.

By segmenting or minimizing the size of the conductive surface the number of electrons in its contribution to the initial shock are also reduced. For example, experimentation with conductive vinyl mats indicates surfaces of 1–2 square feet exhibit much less shock perception than mats of 5 square feet.

Figure 11:
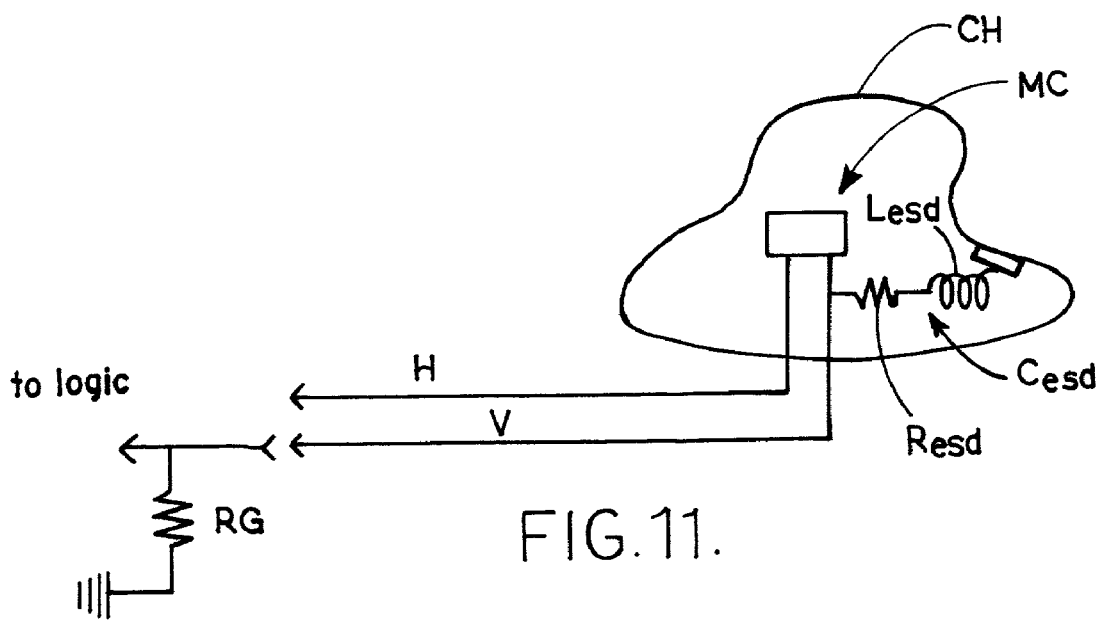
FIG. 11 illustrates a system that utilizes a signal path.

This principle can be understood by referring to the discussion presented in relation to FIG. 11 of the parent application, which is fully incorporated herein by reference. A system includes a contact element that is electrically connected to a ground circuit by plugging a conductor into a grounded connection at plug. The grounded connection is directly connected to earth which contains a large mass of electrons. The conductor, itself, is a source of electrons. Thus, if a person who has built up an ESD charge touches the conductor, the mass of electrons in the ground and in the earth will be available for a shock to that person. A contact device can be a mat or any other object that is likely to be touched by a user. If the contact device is isolated from any mass of electrons, the person touching that device will not receive a shock. However, if there is any mass of electrons available, even if the mass is associated only with the conductor, the person is likely to receive a shock upon touching contact device. However, if the contact device is not electrically connected to some mass of electrons, the person touching contact device will not discharge the electrostatic energy he or she has built up. Therefore, there is a double-edge sword present: there must be some mass of electrons available so a discharge can be effected; however, the mass of electrons must not be so large that a painful shock is felt upon the discharge occurring.

Realizing this, the system embodying the invention disclosed in the parent application electrically connects a contact device to a source of electrons, but does so in a manner that keeps the mass of electrons available to a minimum. The invention achieves this result by placing a resistor physically close to the contact point so some electron mass is available, but not a large electron mass as might be present if the wire itself is present in the discharge circuit. Heretofore, no one has realized that the wire itself might be a source of electrons that produce a shock during ESD. The resistor being physically close, in some cases, within one foot, to the contact point reduces the mass of electrons available to discharge the electrostatic charge on a person. Since the mass of electrons is reduced, the discharge will be slower than if a large mass of electrons is available. Thus, the invention disclosed in the parent application accounts for this by creating a situation where the person contacts the discharge contact on a continuous basis for long periods of time (long with reference to a touch, that is, longer than a touch). The "slow" slight discharge is nearly, if not totally, unnoticed by the person; yet is extremely effective in achieving the ultimate purpose of bleeding the ESD from a person in a non-noticeable manner.

The above concepts are embodied in the present invention in a plug that permits proper and safe grounding of equipment.

Figure 2:
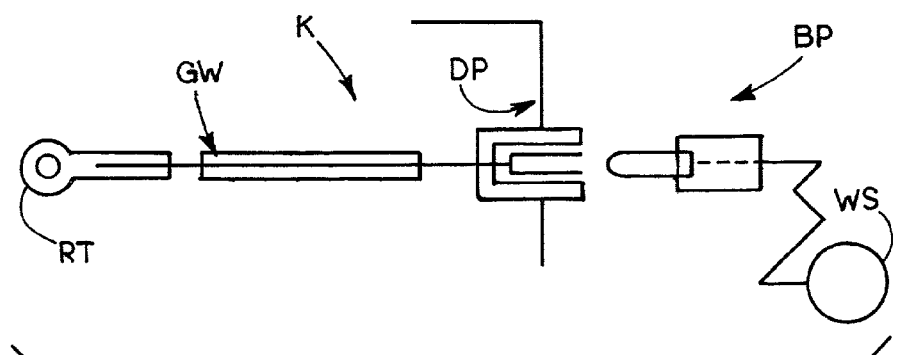
FIG. 2 illustrates a workstation personal grounding kit of the prior art.
Figure 3A:
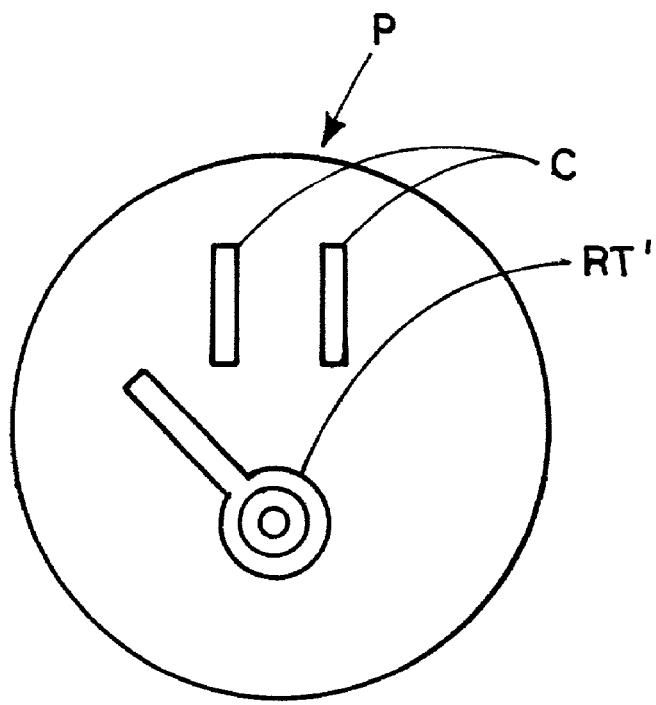
FIG. 3A illustrates a prior art plug having a ring terminal.
Figure 3B:
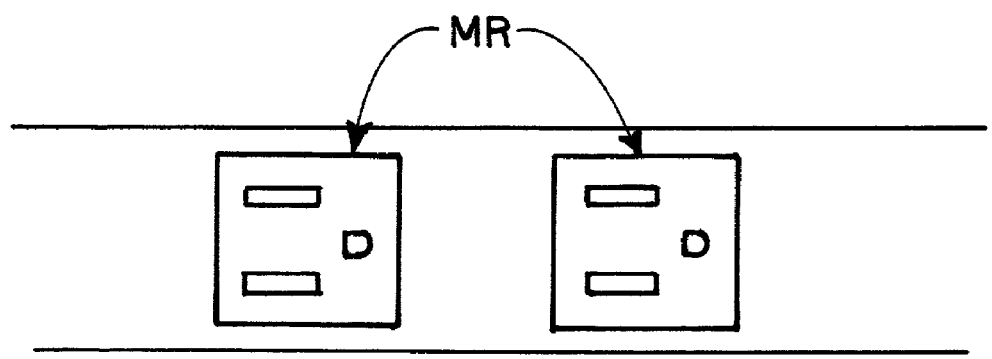
Figure 4A:
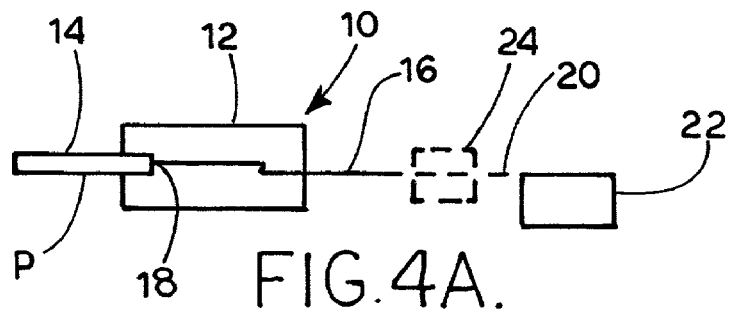
FIG. 4A illustrates a grounding plug with a grounding wire embodying the present invention.

Referring to FIG. 4A, a plug 10 is shown. Plug 10 includes a housing 12 that can be plastic or the like, having a metal prong 14 mounted thereon. Prong 14 is sized and shaped to be accommodated in a ground hole in a receptacle. A wire 16 is electrically connected at one end 18 thereof to ground prong 14 and at another end 20 thereof directly to an element 22 that is to be grounded. Using plug 10, an element can be grounded in a safe and proper manner. Element 22 can include an electrostatic discharge conducting contact element which is in time-extended contact with a person who is to be protected from electrostatic discharge when in use. As also indicated in FIG. 4A, a banana plug quick disconnect or similar connection 24 can be included to make connection of the element being grounded to plug 10 easier. It is noted that the banana connection is shown in FIG. 2. The connection between wire 16 and elment 22 can also be effected using the ring terminal RT shown in FIG. 2 if desired.

Figure 4B:
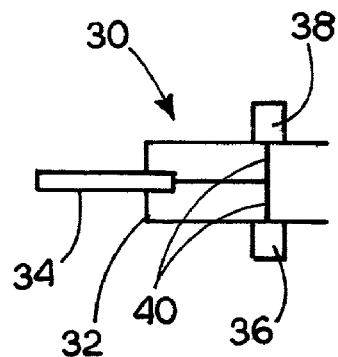
FIG. 4B illustrates a grounding plug with connection tab grounding terminals.
Figure 8A:
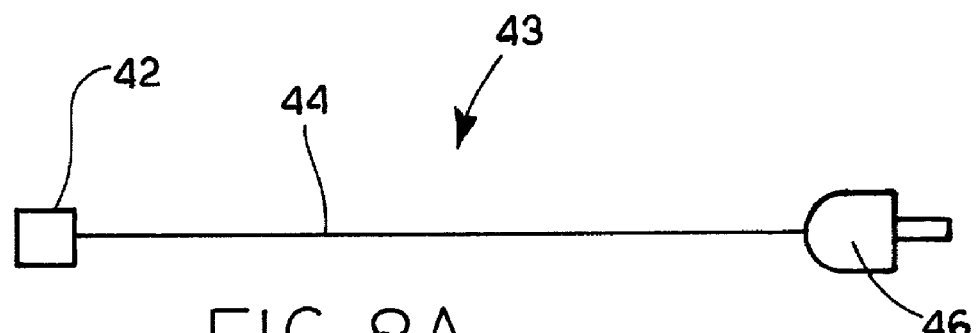
FIG. 8A is a schematic illustrating a ground connection in combination with a quick-disconnect tab.
Figure 8B:
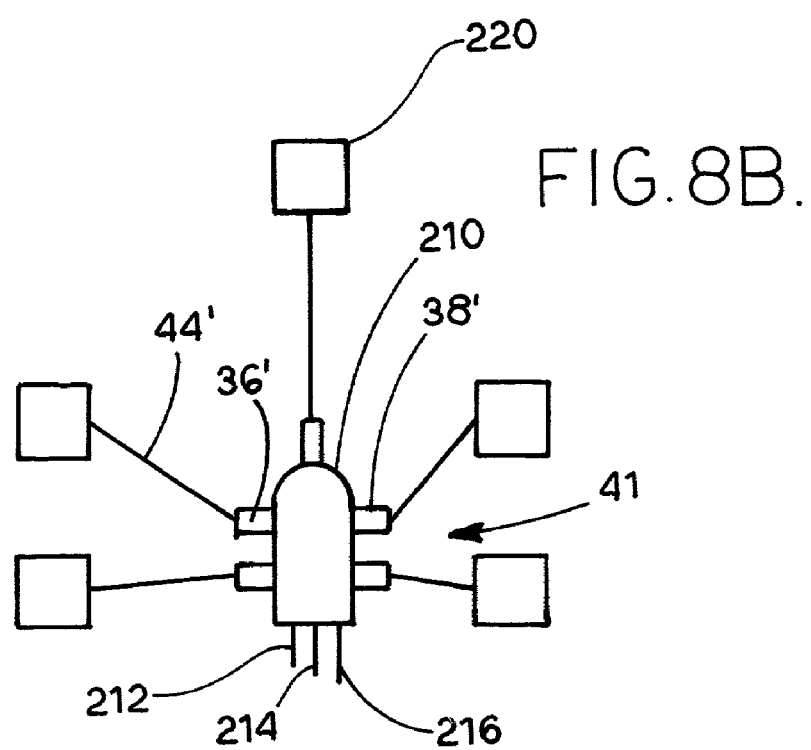
FIG. 8B is a schematic illustrating a ground plug having a plurality of tabs thereon.

A plug 30 is shown in FIG. 4B and inclues a housing 32 on which a ground prong 34 is mounted. A plurality of tabs 36 and 38 are also mounted on housing 32 and are electrically connected to prong 34 by conductors 40 located inside housing 32. Separate elements are connected to ground via tabs 36 and 38, such as indicated in FIG. 8B for plug system 41 which includes tabs such as tabs 36' and 38'. A quick-disconnect tab 42 is shown in FIG. 8A in a plug system 43 and can be electrically connected to one of the tabs 36, 38, 36' or 38' to ground an element that is electrically connected to tab 42 by an electrical connector 44 and a jack type connector 46.

Figure 5A:
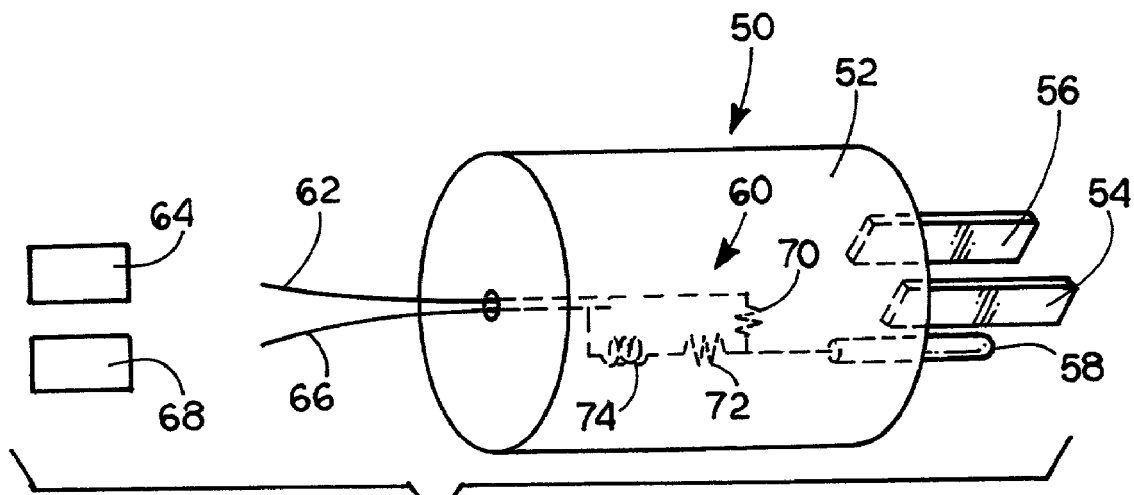
FIG. 5A illustrates plug style grounding element.

A plug 50 is shown in FIG. 5A which is used in connection with multiple grounding wires, each of which is connected to a separate element to be grounded. Plug 50 includes a housing 52 having a plurality of prongs 54 and 56 thereon which are engaged with appropriate holes in a receptacle, and a ground prong 58 which is engaged with a ground hole of a receptacle as above discussed. Inside housing 52, is a circuit 60 which electrically connects the elements to be grounded to ground prong 58. Circuit 60 includes a first electrical conductor 62 electrically connected to a first element 64 and a second electrical conductor 66 which is electrically connected to a second element 68 to be grounded. As shown in FIG. 5A, a first resistor 70 is located inside housing 52 and a second resistor 72 is also located inside housing 52. The resistors serve the function discussed above and in the parent application and thus will not be further discussed. An inductor 74 is also shown in circuit 60 to be in series with resistor 72; however, the inductor could be in series with resistor 70, or a second inductor could be included in circuit 60 to be in series with resistor 70 if desired. The inductor also serves the purpose discussed in the parent application. Plug 50 uses only the grounding conductor of a receptacle and multiple grounding wires are provided. Each of the grounding wires is equipped with circuitry compatible with the grounding needs of the device to be connected to the wires.

It is noted that prongs 54 and 56 serve no electrical function in the case being discussed and, without departing from the scope of the present invention, either or both of the prongs 54 and/or 56 could be either totally eliminated or replaced by non-conductive prongs that serve only to mechanically stabilize plug 50. This is indicated by showing prong 54 as non-conductive material, such as plastic or the like.

Figure 5B:
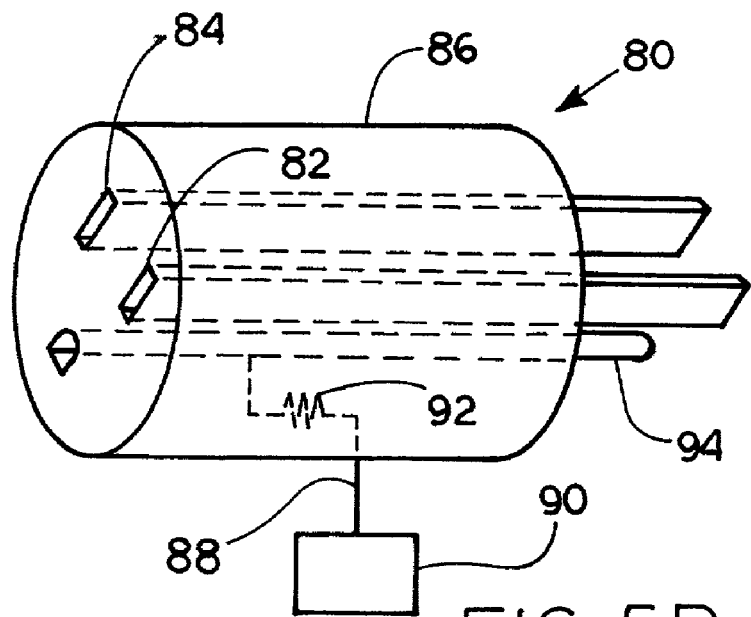
FIG. 5B illustrates a grounding adapter.

A plug 80 is shown in FIG. 5B. Plug 80 has a matching set of female connectors 82 and 84 on one end of housing 86 which are equivalent to the receptacle connectors so a standard device may still be plugged in. Plug 80 will permit use of the same receptacle for a component needing to be plugged in as well as a component that needs grounding. Plug 80 includes an electrical conductor 88 that is electrically connected to an element 90 that is to be grounded and has a resistor 92 electrically connecting conductor 88 to ground prong 94. Other circuit elements, including further resistors or no resistors at all as well as inductors can be included with plug 80 as will occur to those skilled in the art based on the teaching of this disclosure.

Figure 5C:
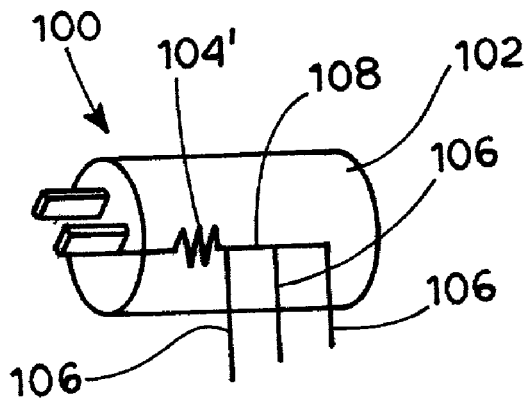
FIG. 5C illustrates an adapter that permits ESD grounding to be achieved with power plugs not incorporating a separate third wire circuit.

A multiple wire grounding adapter 100 is shown in FIG. 5C. Typically, two wire configurations are not used for grounding because there is no grounding conductor. However, in many ESD applications, effective discharge grounding can still be provided because very high series resistances in the 1–100 megohm range are acceptable in the ground path. Adapter 100 includes a housing 102 has a resistor 104 in housing 102 and has a value as determined according to the teaching of the parent disclosure to ensure safety. Multiple connections can be associated with adapter 100 via conductors 106 and 108.

Figure 5D:
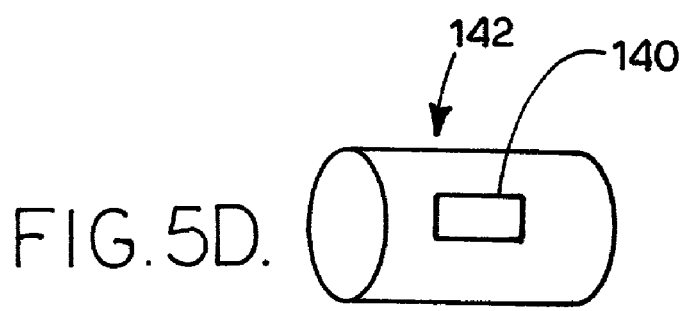
FIG. 5D illustrates an element with a test circuit.

Any of the adapter plugs of the present invention can include a test circuit to verify grounding, power, voltage, or the like. As shown in FIG. 5D, a test circuit 140 is included with a plug 142 and is electrically connected to the circuitry in the plug and/or to the elements being grounded to provide an indicator, either visual or audible, of an incorrect connection. A visual indicator can also be used to indicate a proper connection as well if desired.

Figure 6:
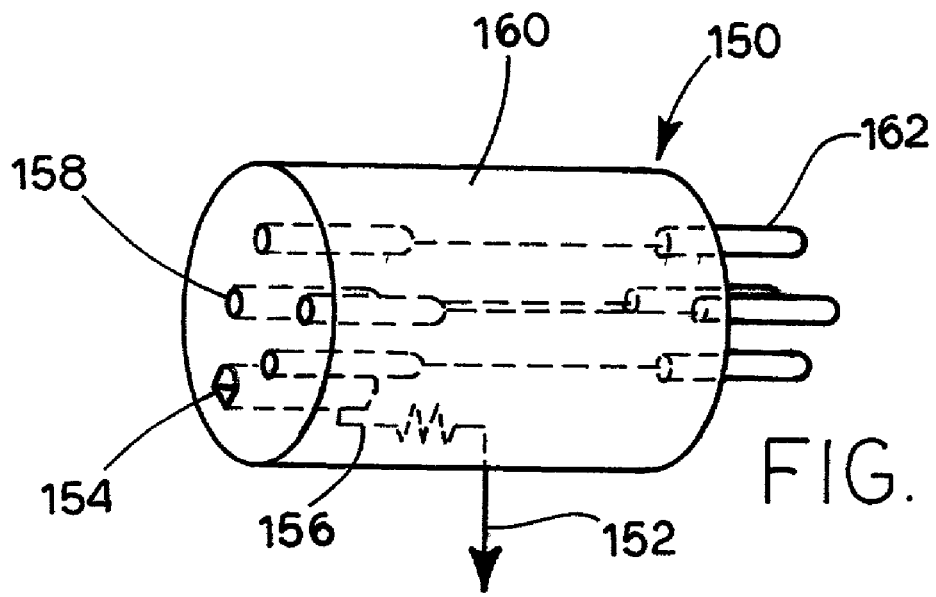
FIG. 6 illustrates a signal plug adapter/external ground.

A signal plug adapter 150 is shown in FIG. 6. Often, grounding may be desired at a device coupled by a signal cable and receptacle which might not include a suitable ground. Adapter 150 includes an external ground source 152 which is electrically connected to a connection 154 by an electrical connector 156 which can have a resistor therein if desired. Suitable female connectors, such as connector 158, are included on housing 160 as are suitable male connectors, such as connector 162.

Figure 7:
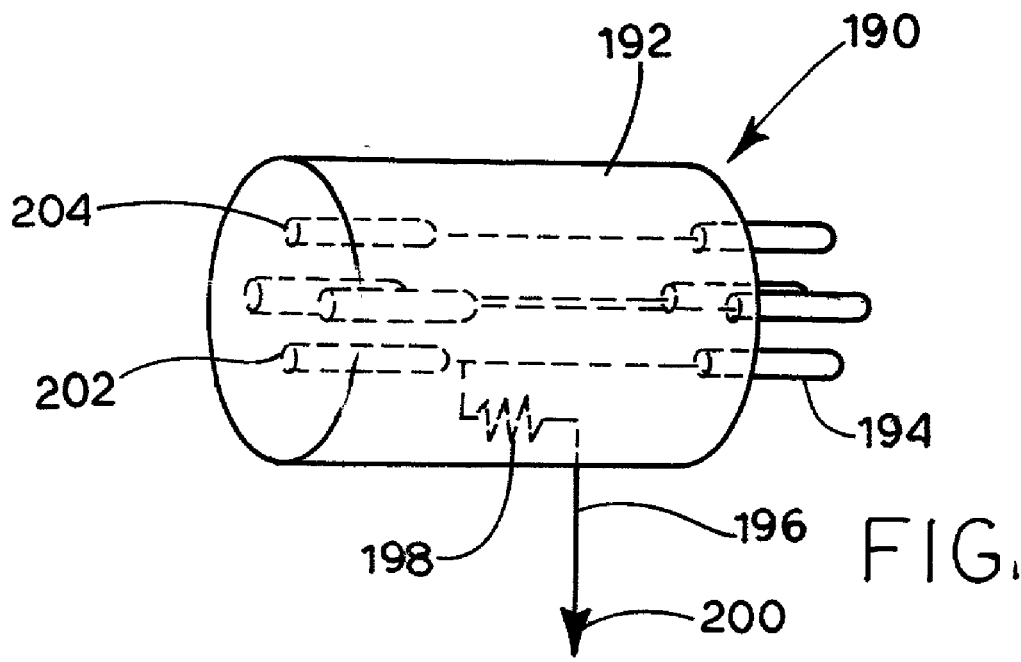
FIG. 7 illustrates a signal plug adapter/internal grounding.

Plug 190 in FIG. 7 is a signal plug adapter with an internal ground. Thus, plug 190 includes a housing 192 having a signal ground prong 194 on one end and an electrical connector 196 connected to prong 194 inside housing 192. A resistor 198 can be included and electrical connector 196 is connected to a suitable ground or to an element that is being grounded as indicated by arrow 200. Female connectors, such as connector 202 and 204, are also included on adapter 190.

Referring again to FIG. 8B, it is seen that plug system 41 includes a housing 210 having a plurality of prongs 212, 214 and 216 thereon, with one of the prongs being a ground prong. The plug also includes circuitry inside the housing as discussed above to connect elements, such as element 220, with ground in the manner discussed above via tabs on the plug housing. As above discussed, tabs, such as tab 42 shown in FIG. 8A, can be connected to tabs, such as tab 36' shown in FIG. 8B with wires, such as wire 44' connected to a component to be grounded via a connector such as connector 46 shown in FIG. 8A.

The inventor has observed that, in certain circumstances, if a very large resistance is inserted into a path followed by ESD, even though a voltage is high, the resulting current is so low that equipment will not be damaged. Thus, for example, if ESD voltage is 10,000 volts but a resistor of 100 megohms is inserted into the circuit, a resulting current of 0.0001 amps occurs. This current is so small that it could be inserted into most signal conductors without being harmful to the device.

Figure 9:
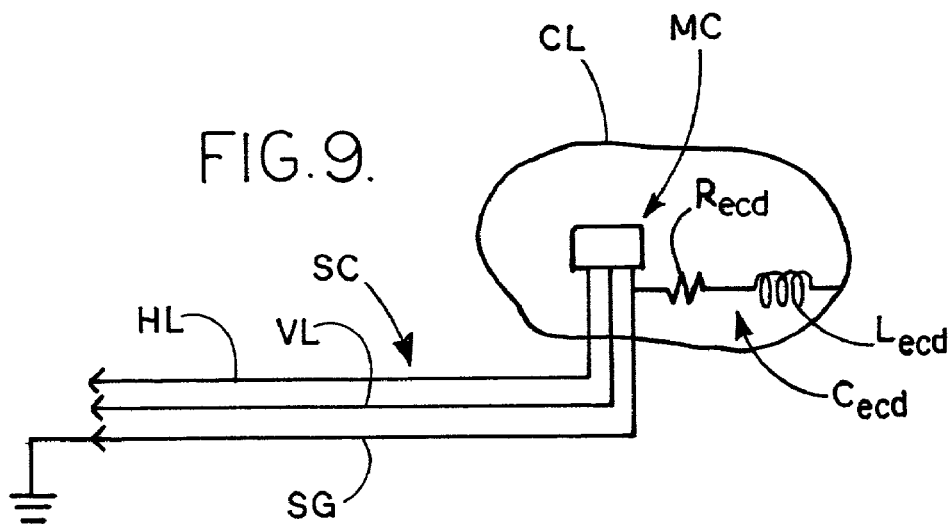
FIG. 9 illustrates a system that utilizes a signal ground.
Figure 10:
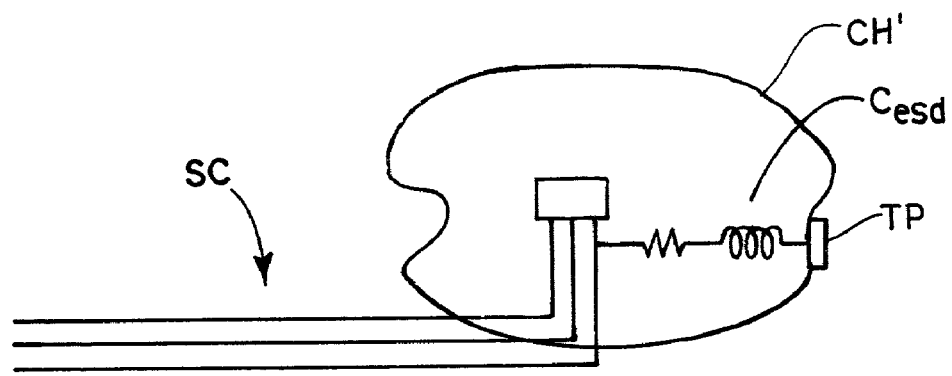
FIG. 10 illustrates another system that utilizes a signal ground.

In accordance with this observation, the present invention can be embodied in a circuit such as shown in FIGS. 9, 10 and 11. As shown in FIG. 9, a circuit $C_{esd}$, comprising a resistor $R_{esd}$ and an inductor $L_{esd}$ can inserted into a circuit MC in a signal device, such as a mouse. The overall resistance of circuit $C_{esd}$ can be 100 megohms. Circuit $C_{esd}$ is connected to the signal device housing CH and to one line of the signal cable SC. As shown in FIG. 9, the line for signal ground, SG is used. Thus, every time a user touches housing CH, ESD can be discharged via circuit $C_{esd}$ and will be so small that no damage will be done to the device connected to signal cable SC. An alternative form of this system is shown in FIG. 10 in which a touchpad TP is incorporated into housing CH'. Touchpad TP is connected to circuit $C_{esd}$ so every time a user touches touchpad TP, the discharge will be through circuit SC but will be so small as to be harmless. It is also noted that the circuit $C_{esd}$ could also be connected to signal leads, such as a vertical lead VL or to a horizontal lead HL if desired in the case of a mouse. Eventually, these leads connect to ground. A further alternative is to include a large resistor, such as a 100 megohm resistor, in the device connected to the signal device. This alternative is shown in FIG. 11 with a resistor $R_G$ installed between the signal lead and ground.

As will be understood, even though FIG. 11 shows a touchpad, the form of the invention in which no touchpad is included can be used in connection with the form shown in FIG. 11.

It is also observed that the just-described large resistor circuit $C_{esd}$ can be used in connection with any of the plugs described hereinabove. In such a case, the large resistor, 100 megohms, is installed between the plug and the equipment to be grounded. The just-described circuit $C_{esd}$ can be used to provide suitable ESD dissipation in cases where there is not a convenient typical low impedance ground present.

It is understood that while certain forms of the present invention have been illustrated and described herein, it is not to be limited to the specific forms or arrangements of parts described and shown.

What is claimed is:

1. A plug comprising:
   a connection element which is connected to a ground system having stray inductance and resistance when in use;
   a connection element which is connected to an electrostatic discharge conducting contact element which is in contact with a person who is to be protected from electrostatic discharge when in use;
   a plug housing;
   at least one electrical prong on said housing;
   a control circuit electrically connected to said contact element, said control circuit including a first resistor element in series with said contact element;
   an inductor element in said plug housing and electrically interposed in series between said contact element and said ground system and which is connected to said ground system at a connection location, said inductor element having an inductance which is greater than the stray inductance of said ground system at the connection location between said inductor element and said ground system connected to said first resistor; and
   said electrical prong being a ground prong electrically connected to said control circuit.

2. The plug defined in claim 1 further including a second resistor in said plug housing and electrically connected to said first resistor.

3. The plug defined in claim 2 wherein said second resistor has a resistance of one megohm.

4. The plug defined in claim 1 further wherein said first resistor is located at least partially in said plug housing.

5. The plug defined in claim 1 wherein said first resistor is physically located closely adjacent to said contact element.

6. The plug defined in claim 1 further including a prong positioned on said plug housing as a hot prong.

7. The plug defined in claim 6 further including a neutral prong positioned on said plug housing as a neutral plug.

8. The plug defined in claim 1 further including female receptacles.

9. The plug defined in claim 1 further including an internal resistor having a value of at least one megohm.

10. The plug defined in claim 1 further including a plurality of grounding connectors.

11. The plug defined in claim 1 further including a plug adapter and the control circuit which is at least partially located in said plug adapter.

12. The plug defined in claim 11 further including an output lead.

13. The plug defined in claim 1 further including a test circuit.

14. A plug comprising:
   A) a connection element which is connected to a ground system having a stray inductance when in use;
   B) a plug housing;
   C) a contact element which is electrically connected to an electrostatic discharge conducting contact element which is in contact with a person who it to be protected from electrostatic discharge when said contact element is in use; and
   D) an inductor element in said plug housing, said inductor element being electrically interposed in series between said contact element and the ground system and which is electrically connected to the ground system at a connection location, said inductor element having an inductance which is greater than the stray inductance of the ground system at the connection location between said inductor element and the ground system.

15. The plug defined in claim 14 further including a resistor element in said plug housing, said resistor element being electrically connected in series with said contact element and being electrically connected to the ground system at a connection location.

16. The plug defined in claim 15 wherein the ground system includes stray resistance and said resistor element has a resistance that is greater than the stray resistance of the ground system at the connection location between the resistor element and the ground system.

17. A plug unit comprising:
   a connection element which is connected to an electrostatic discharge conducting contact element which is in contact with a person who is to be protected from electrostatic discharge when in use;
   a plug housing;
   at least one electrical prong on said plug housing;
   a control circuit electrically connected to said contact element, said control circuit including a first resistor element electrically connected in series with said contact element;
   an inductor element in said plug housing and electrically interposed in series between said contact element and a ground system which has stray inductance and stray resistance, said inductor element being electrically connected to the ground system at a connection location, said inductor element having an inductance which is greater than the stray inductance of the ground system at the connection location between said inductor element and the ground system; and
   said electrical prong being a ground prong electrically connected to said control circuit.

18. The plug defined in claim 17 wherein the resistor element of said control circuit has a resistance that is greater than the stray resistance of the ground system.

19. A plug unit comprising:
   connection element which is connected to an electrostatic discharge conducting contact element which is in contact with a person who is to be protected from electrostatic discharge when in use;
   a plug housing;
   at least one electrical prong on said plug housing;
   an inductor element in said plug housing, said inductor element being electrically interposed in series between said contact element and a ground system which has stray inductance and stray resistance, said inductor element being electrically connected to the ground system at a connection location, said inductor element having an inductance which is greater than the stray inductance of the ground system at the connection location between said inductor element and the ground system; and said electrical prong being a ground prong electrically connected to said control circuit.

20. A plug comprising:
a connection element which is connected to a ground system when in use;
a connection element which is connected to an electrostatic discharge conducting contact element which is in contact with a person who is to be protected from electrostatic discharge when in use;
a plug housing,
at least one electrical prong on said housing;
a control circuit electrically connected to said contact element, said control circuit including a first resistor element in series with said contact element, an inductor element in said plug housing and electrically interposed in series between said contact element and said ground system and which is connected to said ground system at a connection location, wherein the ground system has a stray inductance and said inductor element has an inductance which is greater than the stray inductance of the ground system at the connection location between said inductor element and the ground system; and said electrical prong being a ground prong electrically connected to said control circuit when in use.

* * * * *